United States Patent
Jiang et al.

(10) Patent No.: US 10,906,860 B2
(45) Date of Patent: Feb. 2, 2021

(54) METHOD FOR SYNTHESIZING CHIRAL BETA-HYDROXY ACID ESTER COMPOUND

(71) Applicant: Wenzhou University, Zhejiang (CN)

(72) Inventors: Jun Jiang, Wenzhou (CN); Hongxin Liu, Wenzhou (CN); Na Wang, Wenzhou (CN); Juan Li, Wenzhou (CN)

(73) Assignee: WENZHOU UNIVERSITY, Zhejiang (CN)

( * ) Notice: Subject to any disclaimer, the term of this patent is extended or adjusted under 35 U.S.C. 154(b) by 0 days.

(21) Appl. No.: 16/702,555

(22) Filed: Dec. 4, 2019

(65) Prior Publication Data
US 2020/0190013 A1    Jun. 18, 2020

(30) Foreign Application Priority Data
Dec. 14, 2018 (CN) .......................... 2018 1 1536129

(51) Int. Cl.
*C07C 67/31* (2006.01)
*C07B 53/00* (2006.01)
*B01J 31/18* (2006.01)
*C07C 69/675* (2006.01)

(52) U.S. Cl.
CPC ........... *C07C 67/31* (2013.01); *B01J 31/1815* (2013.01); *C07B 53/00* (2013.01); *B01J 2531/0261* (2013.01); *C07C 69/675* (2013.01)

(58) Field of Classification Search
None
See application file for complete search history.

(56) References Cited

PUBLICATIONS

Baudoux et al. (Green Chemistry, 2010, 12(2), 252).*

* cited by examiner

*Primary Examiner* — Sudhakar Katakam
*Assistant Examiner* — Jennifer C Sawyer
(74) *Attorney, Agent, or Firm* — Leong C. Lei

(57) ABSTRACT

A method for synthesizing a chiral β-hydroxy acid ester compound is disclosed. The method includes the steps of: using an aldehyde compound and a monoalkyl malonate as raw materials, using a metal and a chiral ligand as a catalyst to make the raw materials be directly and fully reacted in an organic solvent and form a reaction solution, and separating and purifying the reaction solution to obtain the highly stereoselective β-hydroxy acid ester compound. The beneficial effects are mainly embodied in: 1. simple operation; 2. rapidly constructing a highly stereoselective β-hydroxy acid ester skeleton structure molecule; 3. high reaction yield and good stereoselectivity. Therefore, the invention has high basic research significance, industrial production value and social economic benefit.

10 Claims, 1 Drawing Sheet

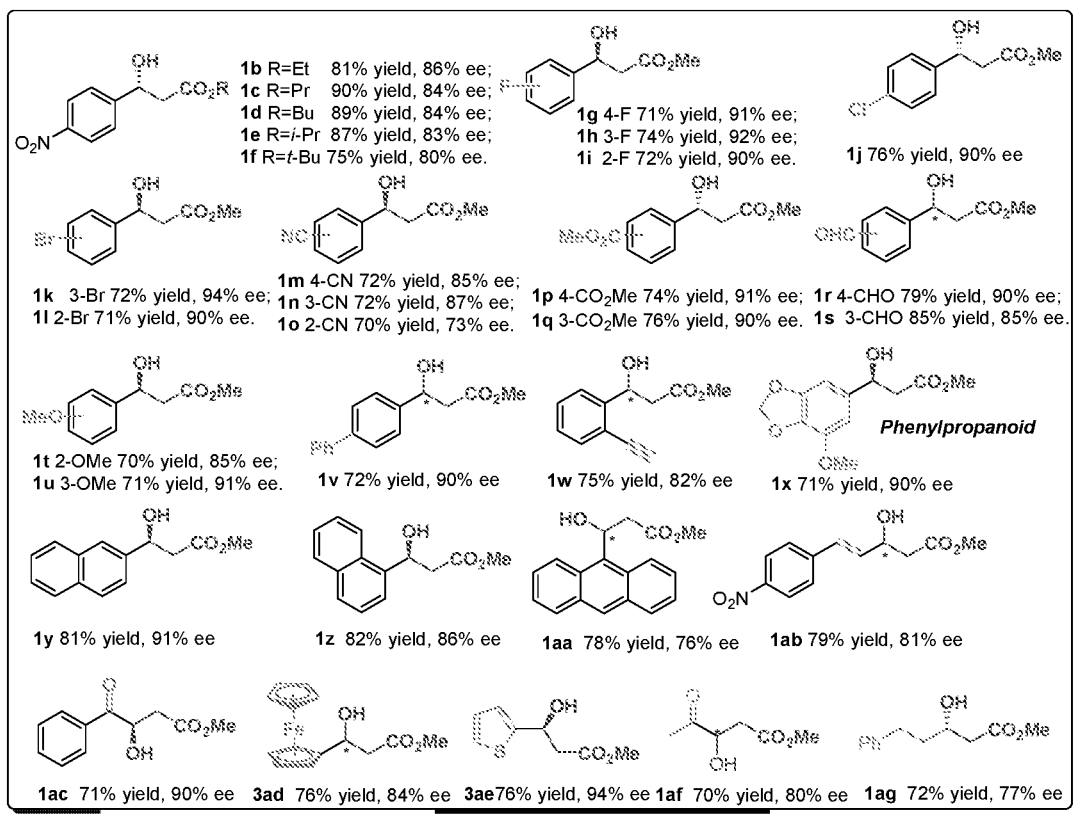

METHOD FOR SYNTHESIZING CHIRAL BETA-HYDROXY ACID ESTER COMPOUND

TECHNICAL FIELD

The present disclosure relates to the field of organic chemistry, in particular to a chiral β-hydroxy acid ester compound and a synthetic method thereof by decarboxylation aldol addition.

BACKGROUND OF RELATED ARTS

Chiral β-hydroxy acid esters and their derivatives are widely present in many natural products and drug molecules, and are important intermediates in organic synthesis and drug development projects. Chiral β-hydroxy acid esters are important precursors for the synthesis of chiral β-hydroxy acids, β-amino acids, penicillins, biopheromones, and the like. Chiral β-hydroxy-substituted carboxylic acid esters are the main body of many natural products (chuckmycin A, aloe acid, etc.) and many drug molecules, especially important synthetic intermediates for antipsychotic and hyperactive psychotropic drugs (fluoxetine, duloxetine, atomoxetine), and the rapid and efficient synthesis of the chiral drug molecule, Phenylpropanoid. Therefore, it is of great significance to develop a green and efficient synthetic strategy for the synthesis of chiral β-substituted carboxylates and their derivatives.

From the existing reports, the chiral β-hydroxy-substituted carboxylic acid esters for constructing important organic synthesis intermediates and the core skeleton of many pharmaceutically active molecules are achieved by asymmetric mukaiyama aldol reaction and asymmetric hydrogenation reduction of β-ketocarboxylate. However, due to the limitations of understanding this type of reaction, there are disadvantages such as the need to construct the substrate in advance, the limited compatibility of the product structure functional groups, and the strict reaction conditions. On this basis, designing and developing a new substrate structure and carrying out the synthesis of a novel type of chiral β-hydroxy acid ester compound have important theoretical research significance and practical application value.

In addition, the existing reports have many limitations, and there are very few reports of the construction of highly stereoselective chiral β-hydroxy acid ester compounds and polyfunctional chiral β-hydroxy acid ester compounds. Based on this, in order to further understand the nature of the decarboxylation addition reaction, expand the type and application of the reaction, and develop a new synthetic route for the chiral β-hydroxy acid ester skeleton structure molecule, which has an important driving force for the development and design of drug molecules and basic methodological research.

SUMMARY OF THE INVENTION

A technical problem to be solved by the embodiments of the present invention is to provide a method for synthesizing a chiral β-hydroxy acid ester compound. The method has the advantages of simple operation, reasonable process, low toxicity, mild reaction condition, high reaction yield, good product quality and high stereoselectivity.

In order to achieve the above object, the technical solution of the present invention is that the method comprises the steps of:

using an aldehyde compound and a monoalkyl malonate as raw materials;

using a metal compound, an organic acid salt and a chiral ligand as a catalyst to make the raw materials carry out decarboxylation aldol addition reaction in an organic solvent;

after the reaction is completed, performing separation and purification to obtain a chiral β-hydroxy acid ester compound, wherein the chiral β-hydroxy acid ester compound has the structural formula as below:

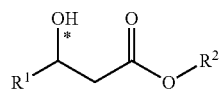

The aldehyde compound has the structural formula as below:

$R^1$—CHO

The monoalkyl malonate has the structural formula as below:

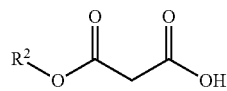

The $R^1$ is selected from one of the group consisting of an alkyl group, a substituted phenyl group or an aryl group having a fluorine, a chlorine, a bromine, a nitro group, an alkyl group, an alkoxy group or the like; the $R^1$ is preferably p-nitrophenyl.

The $R^2$ is selected from one of methyl, ethyl, propyl, butyl, isopropyl, and tert-butyl; the $R^2$ is preferably an alkyl group.

The organic solvent used is an organic solvent that does not react with reactants and products.

Further, the organic solvent is selected from the group of consisting one or a combination of dichloromethane, ethyl acetate, tetrahydrofuran, acetonitrile, toluene, methanol, and chloroform.

Further, the mass of the organic solvent used is 1-200 times the mass of the raw materials, preferably 20-50 times.

Further, the molar ratio of the aldehyde compound to the monoalkyl malonate is 1:1-5, preferably 1:2.

Further, the metal compound in the catalyst is selected from one or a combination of copper triflate, copper sulfate, copper acetate, palladium acetate, ferrous fluoride, silver acetate, nickel acetate tetrahydrate, nickel acetylacetonate, nickel fluoride, nickel chloride hexahydrate, nickel sulfate, nickel perchlorate, and bistriphenylphosphine nickel chloride.

Further, the chiral ligand in the catalyst is selected from one or a combination of the following:

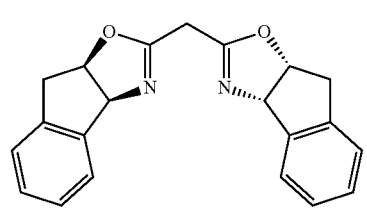

L1

-continued

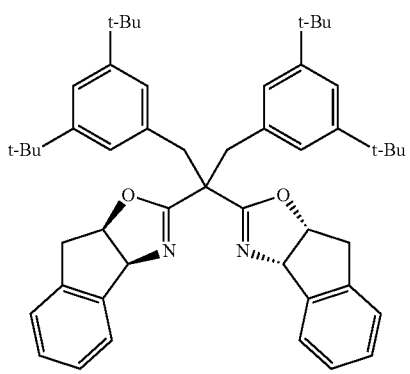
L2

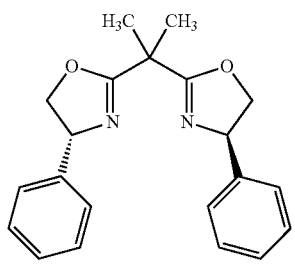
L3

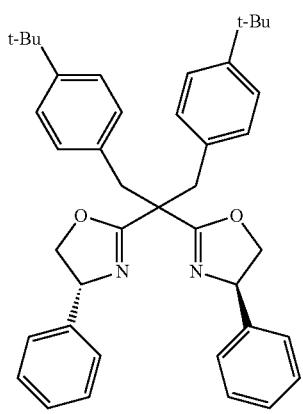
L4

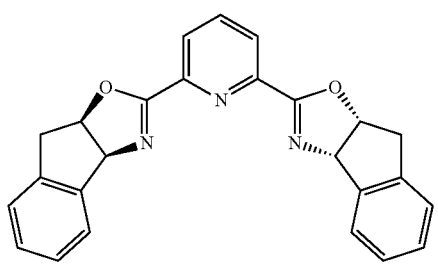
L5

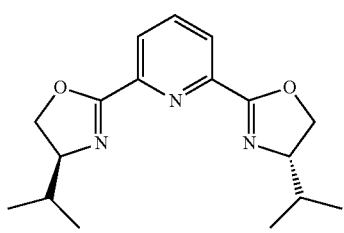
L6

-continued

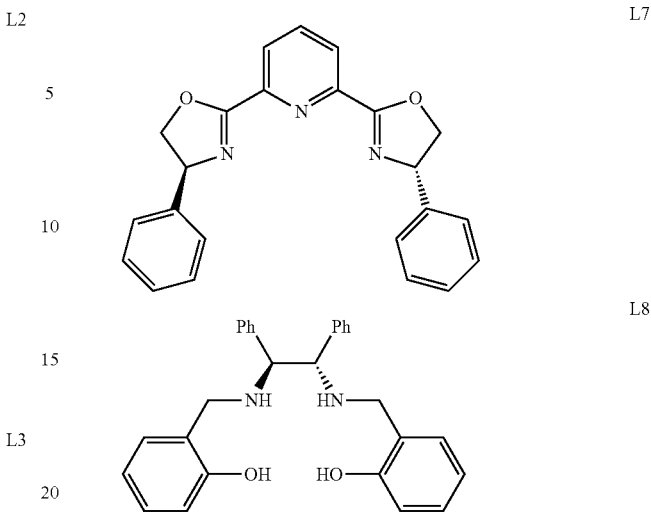
L7

L8 preferably, chiral ligand L5.

Further, the salt in the catalyst is selected from one or a combination of the following:

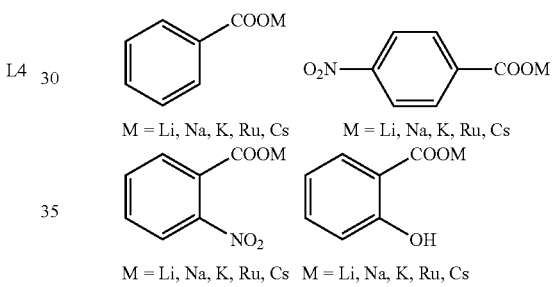

M = Li, Na, K, Ru, Cs    M = Li, Na, K, Ru, Cs

M = Li, Na, K, Ru, Cs    M = Li, Na, K, Ru, Cs

The molar ratio of metal to salt in the catalyst is 1:1-3.

Further, the ratio of the catalyst to the aldehyde compound is 1 wt %-20 wt %, preferably 10 wt %, and the molar ratio of the metal to the chiral ligand in the catalyst is 1:1-1.5, preferably 1:1.1.

In one embodiment of the present invention, the reaction temperature is 0-60° C., preferably 20-30° C., and the reaction time is generally 3-72 hours, preferably 40-60 hours.

The separation and purification described in one embodiment of the present invention is carried out by column chromatography. After the completion of the reaction, the obtained reaction solution is distilled off, and subjected to wet sampling, purified via column chromatography, and dried to obtain the target product β-hydroxyl acid ester compound. Further, the eluent is a mixture of petroleum ether and ethyl acetate, and the ratio of petroleum ether to ethyl acetate is 20:1-2:1, preferably 10:1-5:1.

In a preferred embodiment, the present invention is the first to use a chiral ligand L5 of nickel chloride hexahydrate, potassium o-nitrobenzoate and an oxazoline backbone to catalyze the decarboxylation aldol addition with a monoalkyl malonate, to synthesize a chiral β-hydroxy acid ester compound. The beneficial effects are mainly embodied in: 1. Simple operation; 2. Low cost; 3. High reaction yield; 4. High stereoselectivity. Therefore, the present disclosure has high basic research value and social economic benefits.

BRIEF DESCRIPTION OF THE DRAWINGS

In order to more clearly illustrate the embodiments of the present invention or the technical solutions in the prior art, the drawings used in the embodiments or the description of the prior art will be briefly described below. Obviously, the drawings in the following description are only certain embodiments of the present invention, and it is still within the scope of the present invention for those skilled in the art to obtain other drawings based on these drawings without any inventive labor.

FIG. 1 is a structural diagram of a reaction product in an embodiment of the present invention.

DETAILED DESCRIPTIONS OF EMBODIMENTS

In order to make the objects, technical solutions and advantages of the present invention more apparent, the present invention will be further described in detail with reference to the accompanying drawings.

Preferred Embodiment

The method for chemically synthesizing the chiral β-hydroxyl ester compound according to the present invention is specifically carried out according to the following steps: adding a metal catalyst and an organic acid salt to a reaction vessel under room temperature conditions, sufficiently dissolving with a solvent A, and stirring well 30-60 minutes, adding chiral ligand to the reaction vessel and stirring for 30-60 minutes, then adding common aldehyde and monoalkyl malonate, stirring at 20-30° C. to make the reaction 40-72 hours. In the hours, the progress of the reaction is monitored in real time, and after completion of the reaction, it is separated and purified, and after drying, the target compound of the chiral β-hydroxy acid ester is obtained.

Example 1

The ratio of the amount of the aldehyde having $R^1$ as the para-nitrophenyl group, the monomethyl malonate having IV as the methyl group and the catalyst is 1.0:2.0:0.1. That is, the substrate p-nitrobenzaldehyde 302 mg (2 mmol), malonate monomethyl ester 472 mg (4 mmol), nickel acetate tetrahydrate 49.6 mg (0.2 mmol), chiral ligand L1 72.6 mg (0.22 mmol); the organic solvent is tetrahydrofuran 6.0 g, and the total amount is 20 times that of the substrate p-nitrobenzaldehyde.

The metal catalyst and the chiral ligand L1 are added to the reaction vessel at room temperature, fully dissolved in tetrahydrofuran, stirred well for 30-60 minutes, and then p-nitrobenzaldehyde and monomethyl malonate are added to the reaction vessel. The mixture is stirred at 30° C. for 72 hours to complete the reaction.

After the completion of the reaction, the mixture is separated and purified, and dried to give a white solid, which is 101.3 mg of the desired compound of the chiral β-hydroxy acid ester, the yield is 45%, the enantioselective excess is 2% ee, and the purity is 99.0%. The structure of the desired compound is:

Characterization data:

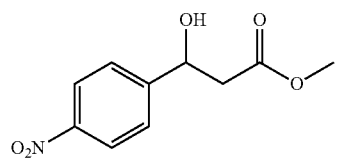

1a

Daicel Chiralpak AS, hexane/iso-propanol=90/10, flow rate 1.0 mL/min, 25° C.: tR (major)=17.1 min, tR (minor)= 21.3 min. 1H NMR (500 MHz, CDCl3) δ 8.20 (d, J=8.7 Hz, 2H), 7.57 (d, J=8.6 Hz, 2H), 5.29-5.20 (m, 1H), 3.76 (d, J=5 Hz, 2H), 3.74 (s, 3H), 2.83-2.69 (in, 2H). 13C NMR (126 MHz, CDCl3) δ 172.27, 149.77, 147.29, 126.52, 123.76, 69.36, 52.10, 42.82.

Example 2

The substrate p-nitrobenzaldehyde 302 mg (2 mmol), malonate monomethyl ester 472 mg (4 mmol), nickel acetate tetrahydrate 49.6 mg (0.2 mmol), chiral ligand L3 73.5 mg (0.22 mmol); the organic solvent is tetrahydrofuran 6.0 g, and the total amount is 20 times that of the substrate p-nitrobenzaldehyde.

The metal catalyst and the chiral ligand L3 are added to the reaction vessel at room temperature, fully dissolved in tetrahydrofuran, stirred well for 30-60 minutes, and then p-nitrobenzaldehyde and monomethyl malonate are added to the reaction vessel. The mixture is stirred at 30° C. for 72 hours to complete the reaction.

The rest processes are the same as those in Example 1, 60.1 mg of the target product 1a is obtained, the yield is 27%, the enantioselective excess is 9% ee, and the purity is 98.8%.

Example 3

The substrate p-nitrobenzaldehyde 302 mg (2 mmol), malonate monomethyl ester 472 mg (4 mmol), nickel acetate tetrahydrate 49.6 mg (0.2 mmol), chiral ligand L5 (4) 86.5 mg (0.22 mmol); the organic solvent is tetrahydrofuran 6.0 g, and the total amount is 20 times that of the substrate p-nitrobenzaldehyde.

The metal catalyst and the chiral ligand L5 are added to the reaction vessel at room temperature, fully dissolved in tetrahydrofuran, stirred well for 30-60 minutes, and then p-nitrobenzaldehyde and monomethyl malonate are added to the reaction vessel. The mixture is stirred at 30° C. for 72 hours to complete the reaction.

The rest processes are the same as those in Example 1, 128.3 mg of the target product 1a is obtained, the yield is 57%, the enantioselective excess is 60% ee, and the purity is 99.8%.

Example 4

The substrate p-nitrobenzaldehyde 302 mg (2 mmol), malonate monomethyl ester 472 mg (4 mmol), nickel acetate tetrahydrate 49.6 mg (0.2 mmol), chiral ligand L5 (4) 86.5 mg (0.22 mmol); the organic solvent is tetrahydrofuran 6.0 g, and the total amount is 20 times that of the substrate p-nitrobenzaldehyde.

The metal catalyst and the chiral ligand L5 are added to the reaction vessel at room temperature, fully dissolved in tetrahydrofuran, stirred well for 30-60 minutes, and then p-nitrobenzaldehyde and monomethyl malonate are added to the reaction vessel. The mixture is stirred at 20° C. for 72 hours to complete the reaction.

The rest processes are the same as those in Example 1, 83.3 mg of the target product 1a is obtained, the yield is 37%, the enantioselective excess is 77% ee, and the purity is 99.6%.

Example 5

The substrate p-nitrobenzaldehyde 302 mg (2 mmol), malonate monomethyl ester 472 mg (4 mmol), nickel acetate 35.2 mg (0.2 mmol), chiral ligand L5 (4) 86.5 mg (0.22 mmol); the organic solvent is tetrahydrofuran 6.0 g, and the total amount is 20 times that of the substrate p-nitrobenzaldehyde.

The metal catalyst and the chiral ligand L5 are added to the reaction vessel at room temperature, fully dissolved in tetrahydrofuran, stirred well for 30-60 minutes, and then p-nitrobenzaldehyde and monomethyl malonate are added to the reaction vessel. The mixture is stirred at 20° C. for 72 hours to complete the reaction.

The rest processes are the same as those in Example 1, 105.8 mg of the target product 1a is obtained, the yield is 47%, the enantioselective excess is 77% ee, and the purity is 99.5%.

Example 6

The substrate p-nitrobenzaldehyde 302 mg (2 mmol), malonate monomethyl ester 472 mg (4 mmol), nickel acetate 35.2 mg (0.2 mmol), o-nitrobenzoic acid sodium salt 75.6 mg (0.4 mmol), chiral ligand L5 (4) 86.5 mg (0.22 mmol); the organic solvent is tetrahydrofuran 6.0 g, and the total amount is 20 times that of the substrate p-nitrobenzaldehyde.

At room temperature, the metal catalyst and o-nitrobenzoic acid sodium salt are added to the reaction vessel, and after fully dissolving with tetrahydrofuran, the mixture is stirred for 30-60 minutes, and then the chiral ligand L5 (4) is further stirred in the reaction vessel. After 30-60 minutes, a common aldehyde and a monoalkyl malonate are then added, and the mixture is stirred at 20° C. for 24 hours to complete the reaction.

The rest processes are the same as those in Example 1, 119.3 mg of the target product 1a is obtained, the yield is 53%, the enantioselective excess is 80% ee, and the purity is 99.2%.

Example 7

The substrate p-nitrobenzaldehyde 302 mg (2 mmol), malonate monomethyl ester 472 mg (4 mmol), nickel chloride hexahydrate 47.2 mg (0.2 mmol), o-nitrobenzoic acid sodium salt 75.6 mg (0.4 mmol), chiral ligand L5 (4) 86.5 mg (0.22 mmol); the organic solvent is tetrahydrofuran 6.0 g, and the total amount is 20 times that of the substrate p-nitrobenzaldehyde.

The rest processes are the same as those in Example 1, 121.5 mg of the target product 1a is obtained, the yield is 54%, the enantioselective excess is 88% ee, and the purity is 99.7%.

Example 8

The substrate p-nitrobenzaldehyde 302 mg (2 mmol), malonate monomethyl ester 472 mg (4 mmol), nickel chloride hexahydrate 47.2 mg (0.2 mmol), o-nitrobenzoic acid potassium salt 82 mg (0.4 mmol), chiral ligand L5 (4) 86.5 mg (0.22 mmol); the organic solvent is 6.0 g of tetrahydrofuran, and the total amount is 20 times that of the substrate p-nitrobenzaldehyde.

The rest processes are the same as those in Example 6, 126 mg of the target product 1a is obtained, the yield is 56%, the enantioselective excess is 90% ee, and the purity is 99.3%.

Example 9

The substrate p-nitrobenzaldehyde 302 mg (2 mmol), malonate monomethyl ester 472 mg (4 mmol), nickel chloride hexahydrate 47.2 mg (0.2 mmol), o-nitrobenzoic acid sodium salt 82 mg (0.4 mmol), chiral ligand L5 (4) 86.5 mg (0.22 mmol); the organic solvent is tetrahydrofuran 6.0 g, and the total amount is 20 times that of the substrate p-nitrobenzaldehyde.

At room temperature, the metal catalyst and o-nitrobenzoic acid sodium salt are added to the reaction vessel, and after fully dissolving with tetrahydrofuran, the mixture is stirred for 30-60 minutes, and then the chiral ligand L5 (4) is further stirred in the reaction vessel. After 30-60 minutes, a common aldehyde and a monoalkyl malonate are then added, and the mixture is stirred at 15° C. for 60 hours to complete the reaction.

The rest processes are the same as those in Example 1, 200.3 mg of the target product 1a is obtained, the yield is 89%, the enantioselective excess is 92% ee, and the purity is 99.6%.

Example 10-41, Corresponding Product 1b-1-Ag

The substrate is an aldehyde (2 mmol) with different substituents, a monoalkyl malonate (4 mmol), nickel chloride hexahydrate 47.2 mg (0.2 mmol), o-nitrobenzoic acid sodium salt 82 mg (0.4 mmol), chiral ligand L5 (4) 86.5 mg (0.22 mmol); the organic solvent is tetrahydrofuran, and the total amount is 20 times that of the substrate p-nitrobenzaldehyde.

At room temperature, the metal catalyst and o-nitrobenzoic acid sodium salt are added to the reaction vessel, and after fully dissolving with tetrahydrofuran, the mixture is stirred for 30-60 minutes, and then the chiral ligand L5 (4) is further stirred in the reaction vessel. After 30-60 minutes, a common aldehyde and a monoalkyl malonate are then added, and the mixture is stirred at 15° C. for 60 hours to complete the reaction.

The rest processes are the same as in Example 1, and the target product 1 is obtained. The result is shown in FIG. 1:

Specific characterization data for Examples 9-41 (1a-1ag):

Example 9

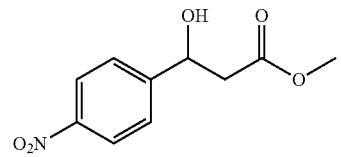 [SMILES: COC(=O)CC(O)c1ccc([N+](=O)[O-])cc1]

Methyl 3-hydroxy-3-(4-nitrophenyl)propanoate (1a)

89% yield, $[\alpha]_D^{25}$=+18.97 (c=0.26 in $CHCl_3$), enantiomeric excess: 92%, Daicel Chiralpak AS, hexane/iso-propanol=90/10, flow rate 1.0 mL/min, 25° C.: $t_R$ (major)=17.1 min, $t_R$ (minor)=21.3 min. $^1$H NMR (500 MHz, CDCl$_3$) δ 8.20 (d, J=8.7 Hz, 2H), 7.57 (d, J=8.6 Hz, 2H), 5.29-5.20 (m, 1H), 3.76 (d, J=5 Hz, 2H), 3.74 (s, 3H), 2.83-2.69 (m, 2H). $^{13}$C NMR (126 MHz, CDCl$_3$) δ 172.27, 149.77, 147.29, 126.52, 123.76, 69.36, 52.10, 42.82.

Example 10

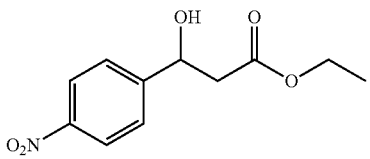

Ethyl 3-hydroxy-3-(4-nitrophenyl)propanoate (1b)

81% yield, [α]D$^{25}$=+21.92 (c=0.26 in CHCl$_3$), enantiomeric excess: 86%, Daicel Chiralpak AS, hexane/iso-propanol=90/10, flow rate 1.0 mL/min, 25° C.: $t_R$ (minor)=13.4 min, $t_R$ (major)=17.8 min. $^1$H NMR (500 MHz, CDCl$_3$) δ 8.17 (d, J=8.7 Hz, 2H), 7.54 (d, J=8.6 Hz, 2H), 5.21 (dt, J=7.9, 3.8 Hz, 1H), 4.16 (q, J=7.1 Hz, 2H), 3.78 (d, J=3.6 Hz, 1H), 2.83-2.58 (m, 2H), 1.24 (t, J=7.1 Hz, 3H). $^{13}$C NMR (126 MHz, CDCl$_3$) δ 171.90, 149.82, 147.43, 126.52, 123.73, 69.38, 61.20, 42.98, 14.09.

Example 11

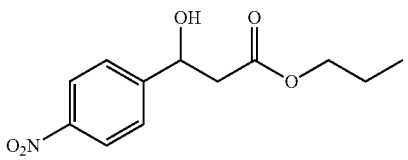 [SMILES: CCCOC(=O)CC(O)c1ccc([N+](=O)[O-])cc1]

Propyl 3-hydroxy-3-(4-nitrophenyl)propanoate (3c)

90% yield; [α]$_D^{25}$=−17.88 (c=0.38 in CHCl$_3$), enantiomeric excess: 84%, Daicel Chiralpak AS, hexane/iso-propanol=90/10, flow rate 1.0 mL/min, 25° C.: $t_R$ (minor)=10.4 min, $t_R$ (major)=14.3 min. $^1$H NMR (500 MHz, CDCl$_3$) δ 8.17 (d, J=8.7 Hz, 2H), 7.54 (d, J=8.7 Hz, 2H), 5.21 (s, 1H), 4.06 (t, J=6.7 Hz, 2H), 3.79 (s, 1H), 2.83-2.57 (m, 2H), 1.67-1.47 (m, 2H), 0.90 (t, J=7.4 Hz, 3H). $^{13}$C NMR (126 MHz, CDCl$_3$) δ 172.00, 149.84, 147.41, 126.53, 123.72, 69.38, 66.78, 42.94, 21.84, 10.26.

Example 12

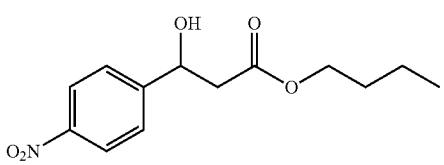 [SMILES: CCCCOC(=O)CC(O)c1ccc([N+](=O)[O-])cc1]

Butyl 3-hydroxy-3-(4-nitrophenyl)propanoate (1d)

89% yield, [α]$_D^{25}$=−17.77 (c=0.69 in CHCl$_3$), enantiomeric excess: 84%, Daicel Chiralpak AS, hexane/iso-propanol=90/10, flow rate 1.0 mL/min, 25° C.: $t_R$ (minor)=8.8 min, $t_R$ (major)=10.6 min. $^1$H NMR (500 MHz, CDCl$_3$) δ 8.18 (d, J=8.4 Hz, 2H), 7.54 (d, J=8.4 Hz, 2H), 5.21 (dd, J=7.9, 3.8 Hz, 1H), 4.11 (t, J=6.7 Hz, 2H), 3.77 (d, J=3.6 Hz, 1H), 2.78-2.65 (m, 2H), 1.62-1.52 (m, 2H), 1.38-1.28 (m, 2H), 0.90 (t, J=7.4 Hz, 3H). $^{13}$C NMR (126 MHz, CDCl$_3$) δ 171.98, 149.81, 147.43, 126.52, 123.72, 69.39, 65.08, 42.95, 30.50, 19.03, 13.59.

Example 13

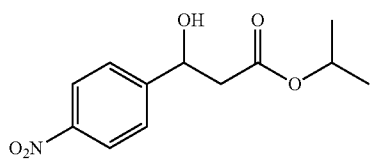 [SMILES: CC(C)OC(=O)CC(O)c1ccc([N+](=O)[O-])cc1]

Isopropyl 3-hydroxy-3-(4-nitrophenyl)propanoate (1e): 87% yield, [α]$_D^{25}$=−34.84 (c=0.26 in CHCl$_3$), enantiomeric excess: 83%, Daicel Chiralpak AD, hexane/iso-propanol=95/5, flow rate 1.0 mL/min, 25: $t_R$ (major)=19.7 min, $t_R$ (minor)=22.1 min. $^1$H NMR (500 MHz, CDCl$_3$) δ 8.19 (d, J=8.7 Hz, 2H), 7.55 (d, J=8.5 Hz, 2H), 5.24-5.17 (m, 1H), 5.05 (dt, J=12.5, 6.3 Hz, 1H), 3.78 (d, J=3.1 Hz, 1H), 2.78-2.60 (m, 2H), 1.23 (dd, J=7.7, 6.6 Hz, 6H). $^{13}$C NMR (126 MHz, CDCl$_3$) δ 171.50, 149.80, 147.15, 126.52, 123.73, 69.41, 68.95, 43.17, 21.74, 21.72.

Example 14

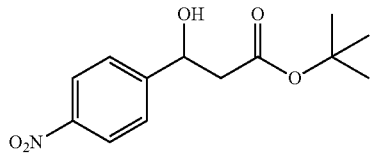 [SMILES: CC(C)(C)OC(=O)CC(O)c1ccc([N+](=O)[O-])cc1]

Tert-butyl 3-hydroxy-3-(4-nitrophenyl)propanoate (1f)

75% yield, [α]$_D^{25}$=−49.62 0.13 in CHCl$_3$), enantiomeric excess: 80%, Daicel Chiralpak AD, hexane/iso-propanol=95/5, flow rate 1.0 mL/min, 25° C.: $t_R$ (major)=20.2 min, $t_R$ (minor)=22.5 min. $^1$H NMR (500 MHz, CDCl$_3$) δ 8.20 (d, J=8.7 Hz, 2H), 7.55 (d, J=8.7 Hz, 2H), 5.17 (d, J=7.8 Hz, 1H), 3.85 (s, 1H), 2.65 (qd, J=16.6, 6.3 Hz, 2H), 1.45 (s, 9H). $^{13}$C NMR (126 MHz, CDCl$_3$) δ 171.41, 149.89, 147.40, 126.52, 123.69, 82.20, 69.49, 43.81, 28.05.

Example 15

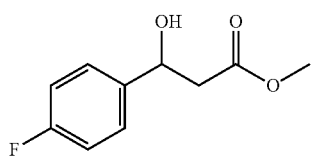

Methyl 3-(4-fluorophenyl)-3-hydroxypropanoate (1g)

71% yield, $[\alpha]_D^{25}$=−20.41 (c=0.29 in CHCl$_3$), enantiomeric excess: 91%, Daicel Chiralpak OD, hexane/iso-propanol=95/5, flow rate 1.0 mL/min, 25° C.: $t_R$ (major)=11.1 min, $t_R$ (minor)=14.5 min. $^1$H NMR (500 MHz, CDCl$_3$) δ 7.33 (dd, J=8.0, 5.6 Hz, 2H), 7.02 (t, J=8.6 Hz, 2H), 5.10 (t, 1H), 3.70 (s, 3H), 3.39 (d, J=2.6 Hz, 1H), 2.70 (qd, J=16.3, 6.4 Hz, 2H). $^{13}$C NMR (126 MHz, CDCl$_3$) δ 172.58, 163.30, 161.34, 138.33, 127.39, 127.33, 115.45, 115.28, 69.68, 51.85, 43.19.

Example 16

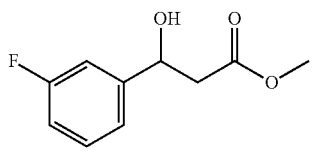

Methyl 3-(3-fluorophenyl)-3-hydroxypropanoate (1h)

74% yield, $[\alpha]_D^{25}$=−41.61 (c=0.26 in CHCl$_3$), enantiomeric excess: 92%, Daicel Chiralpak OD, hexane/iso-propanol=95/5, flow rate 1.0 mL/min, 25° C.: $t_R$ (major)=11.2 min, $t_R$ (minor)=26.8 min. $^1$H NMR (500 MHz, CDCl$_3$) δ 7.19 (dd, J=13.9, 7.1 Hz, 1H), 7.00 (t, J=8.2 Hz, 2H), 6.86 (td, J=8.5, 2.3 Hz, 1H), 5.06-4.94 (m, 1H), 3.70 (d, J=3.7 Hz, 1H), 3.59 (s, 3H), 2.65-2.54 (m, 2H). $^{13}$C NMR (126 MHz, CDCl$_3$) δ 172.46, 163.91, 161.96, 145.45, 145.40, 130.07, 130.00, 121.23, 121.20, 114.61, 114.45, 112.76, 112.59, 69.64, 69.62, 51.87, 43.15.

Example 17

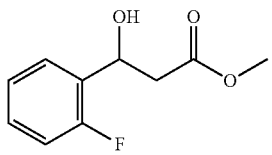

Methyl 3-(2-fluorophenyl)-3-hydroxypropanoate (1i)

72% yield, $[\alpha]_D^{25}$=−62.79 (c=0.26 in CDCl$_3$), enantiomeric excess: 90%, Daicel Chiralpak OD, hexane/iso-propanol=95/5, flow rate 1.0 mL/min, 25° C.: $t_R$ (major)=8.5 min, $t_R$ (minor)=24.3 min. $^1$H NMR (500 MHz, CDCl$_3$) δ 7.42 (dd, J=10.8, 4.2 Hz, 1H), 7.15 (dt, J=13.4, 7.2 Hz, 1H), 7.04 (t, J=7.5 Hz, 1H), 6.94-6.85 (m, 1H), 5.35-5.24 (m, 1H), 3.72-3.63 (m, 3H), 3.59 (s, 3H), 2.64 (qd, J=16.3, 6.3 Hz, 2H). $^{13}$C NMR (126 MHz, CDCl$_3$) δ 172.58, 160.41, 158.46, 129.72, 129.62, 129.14, 129.08, 127.25, 127.22, 124.35, 124.32, 115.28, 115.11, 64.52, 64.50, 51.83, 41.89.

Example 18

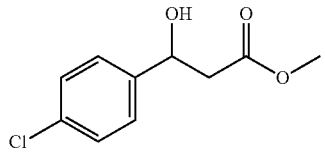

Methyl 3-(4-chlorophenyl)-3-hydroxypropanoate (1j)

76% yield, $[\alpha]_D^{25}$=−44.17 (c=0.37 in CHCl$_3$), enantiomeric excess: 90%, Daicel Chiralpak OB, hexane/iso-propanol=95/5, flow rate 1.0 mL/min, 25° C.: $t_R$ (minor)=15.0 min, $t_R$ (major)=16.7 min. $^1$H NMR (500 MHz, CDCl$_3$) δ 7.41-7.22 (m, 4H), 5.24-4.93 (m, 1H), 3.71 (s, 3H), 3.52-3.46 (m, 1H), 2.79-2.61 (m, 2H). $^{13}$C NMR (126 MHz, CDCl$_3$) δ 172.54, 141.07, 133.50, 128.69, 127.07, 69.62, 51.94, 43.08.

Example 19

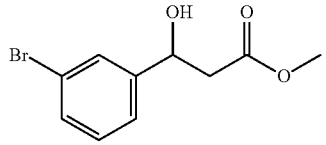

Methyl 3-(3-bromophenyl)-3-hydroxypropanoate (1k)

72% yield, $[\alpha]_D^{25}$=−46.40 (c=0.52 in CHCl$_3$), enantiomeric excess: 94%, Daicel Chiralpak OD, hexane/iso-propanol=95/5, flow rate 1.0 mL/min, 25° C.: $t_R$ (major)=12.4 min, $t_R$ (minor)=41.2 min. $^1$H NMR (500 MHz, CDCl$_3$) δ 7.53 (s, 1H), 7.40 (d, J=7.8 Hz, 1H), 7.27 (d, J=7.6 Hz, 1H), 7.21 (t, J=7.8 Hz, 1H), 5.13-5.05 (m, 1H), 3.71 (s, 3H), 3.58 (s, 1H), 2.75-2.64 (m, 2H). $^{13}$C NMR (126 MHz, CDCl$_3$) δ 172.47, 144.92, 130.85, 130.12, 128.86, 124.28, 122.67, 69.59, 51.95, 43.08

Example 20

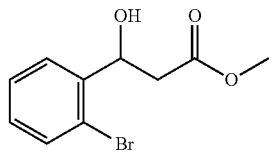

Methyl 3-(2-bromophenyl)-3-hydroxypropanoate (1l)

71% yield, $[\alpha]_D^{25}$=−41.67 (c=0.25 in CHCl$_3$), enantiomeric excess: 90%, Daicel Chiralpak OD, hexane/iso-propanol=95/5, flow rate 1.0 mL/min, 25° C.: $t_R$ (major)=14.0 min, $t_R$ (minor)=41.0 min. $^1$H NMR (500 MHz, CDCl$_3$) δ 7.60 (dd, J=7.8, 1.2 Hz, 1H), 7.52-7.42 (m, 1H), 7.33 (t, J=7.4 Hz, 1H), 7.12 (td, J=7.8, 1.5 Hz, 1H), 5.43 (dd, J=9.8, 2.2 Hz, 1H), 3.72 (s, 3H), 3.68 (s, 1H), 2.85 (dd, J=16.5, 2.6 Hz, 1H), 2.55 (dd, J=16.5, 9.8 Hz, 1H). $^{13}$C NMR (126 MHz, CDCl$_3$) δ 172.71, 141.53, 132.65, 129.10, 127.84, 127.33, 121.40, 69.25, 51.95, 41.47.

Example 21

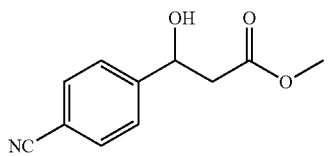

Methyl 3-(4-cyanophenyl)-3-hydroxypropanoate (1m)

72% yield, $[α]_D^{25}$=−44.73 (c=0.16 in CHCl$_3$), enantiomeric excess: 85%, Daicel Chiralpak AD, hexane/iso-propanol=90/10, flow rate 1.0 mL/min, 25° C.: $t_R$ (major)=15.3 min, $t_R$ (minor)=16.0 min. $^1$H NMR (500 MHz, CDCl$_3$) δ 7.64 (d, J=8.1 Hz, 2H), 7.50 (d, J=8.1 Hz, 2H), 5.19 (t, J=6.4 Hz, 1H), 3.72 (s, 3H), 2.72 (d, J=6.4 Hz, 2H). $^{13}$C NMR (126 MHz, CDCl$_3$) δ 172.24, 147.94, 132.36, 126.42, 118.65, 111.47, 69.51, 52.05, 42.89.

Example 22

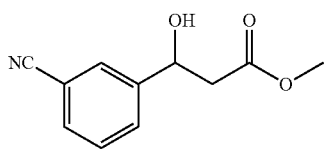

Methyl 3-(3-cyanophenyl)-3-hydroxypropanoate (1n)

72% yield, $[α]_D^{25}$=−45.97 (c=0.34 in CHCl$_3$), enantiomeric excess: 87%, Daicel Chiralpak AD, hexane/iso-propanol=90/10, flow rate 1.0 mL/min, 25° C.: $t_R$ (minor)=12.5 min, $t_R$ (major)=14.3 min. $^1$H NMR (500 MHz, CDCl$_3$) δ 7.69 (s, 1H), 7.60 (d, J=7.8 Hz, 1H), 7.57 (d, J=7.7 Hz, 1H), 7.46 (t, J=7.7 Hz, 1H), 5.15 (d, J=1.6 Hz, 1H), 3.72 (s, 3H), 3.63 (d, J=2.7 Hz, 1H), 2.71 (d, J=6.4 Hz, 2H). $^{13}$C NMR (126 MHz, CDCl$_3$) δ 172.34, 144.07, 131.40, 130.14, 129.41, 129.35, 118.64, 112.67, 69.24, 52.07, 42.87.

Example 23

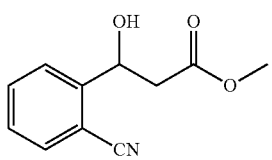

Methyl 3-(2-cyanophenyl)-3-hydroxypropanoate (1o)

70% yield, $[α]_D^{25}$=−50.67 (c=0.13 in CHCl$_3$), enantiomeric excess: 73%, Daicel Chiralpak OD, hexane/iso-propanol=95/5, flow rate 1.0 mL/min, 25° C.: $t_R$ (minor)=23.0 min, $t_R$ (major)=25.4 min. $^1$H NMR (500 MHz, CDCl$_3$) δ 7.86 (d, J=7.5 Hz, 1H), 7.58 (t, J=7.5 Hz, 1H), 7.50 (t, J=7.4 Hz, 1H), 7.42 (d, J=7.6 Hz, 1H), 6.91 (s, 1H), 4.93 (dd, J=10.5, 3.0 Hz, 1H), 3.78 (s, 3H), 3.03 (dd, J=17.1, 3.4 Hz, 1H), 2.47 (dd, J=17.0, 10.6 Hz, 1H). $^{13}$C NMR (126 MHz, CDCl$_3$) δ 171.48, 170.47, 146.01, 132.00, 131.91, 128.58, 123.96, 122.38, 52.99, 52.15, 39.34.

Example 24

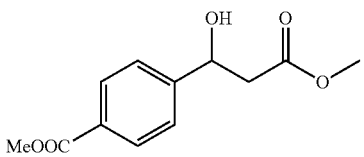 [SMILES: COC(=O)CC(O)c1ccc(C(=O)OC)cc1]

Methyl 4-(1-hydroxy-3-methoxy-3-oxopropyl)benzoate (1p)

74% yield, $[α]_D^{25}$=−32.39 (c=0.21 in CHCl$_3$), enantiomeric excess: 91%, Daicel Chiralpak OD, hexane/iso-propanol=95/5, flow rate 1.0 mL/min, 25° C.: $t_R$ (minor)=20.3 min, $t_R$ (major)=23.4 min. $^1$H NMR (500 MHz, CDCl$_3$) δ 7.99 (d, J=8.1 Hz, 2H), 7.43 (d, J=8.4 Hz, 2H), 5.17 (s, 1H), 3.89 (s, 3H), 3.70 (s, 3H), 3.53 (s, 1H), 2.77-2.68 (m, 2H). $^{13}$C NMR (126 MHz, CDCl$_3$) δ 172.02, 166.83, 147.60, 129.86, 129.60, 125.59, 69.87, 52.07, 51.93, 42.99.

Example 25

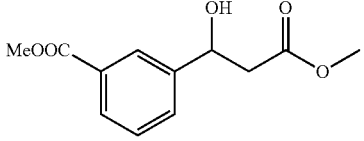 [SMILES: COC(=O)CC(O)c1cccc(C(=O)OC)c1]

Methyl 3-(1-hydroxy-3-methoxy-3-oxopropyl)benzoate (1q)

76% yield, $[α]_D^{25}$=−55.47 (c=0.14 in CHCl$_3$), enantiomeric excess: 90%, Daicel Chiralpak AD, hexane/iso-propanol=90/10, flow rate 1.0 mL/min, 25° C.: $t_R$ (minor)=14.9 min, $t_R$ (major)=18.5 min. $^1$H NMR (500 MHz, CDCl3) δ 8.02 (s, 1H), 7.97-7.88 (m, 1H), 7.58 (d, J=7.5 Hz, 1H), 7.41 (t, J=7.7 Hz, 1H), 5.17 (dd, J=8.4, 4.3 Hz, 1H), 3.89 (d, J=0.7 Hz, 3H), 3.70 (s, 3H), 2.79-2.68 (m, 2H). $^{13}$C NMR (126 MHz, CDCl3) δ 172.55, 166.90, 143.00, 130.44, 130.23, 128.99, 128.67, 126.85, 69.85, 52.13, 51.93, 43.07.

Example 26

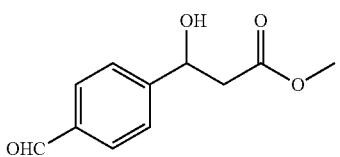

Methyl 3-(4-formylphenyl)-3-hydroxypropanoate (1r)

79% yield, $[\alpha]_D^{25}=-32.93$ (c=0.50 in CHCl$_3$), enantiomeric excess: 90%, Daicel Chiralpak OD, hexane/iso-propanol=90/10, flow rate 1.0 mL/min, 25° C.: $t_R$ (major)=15.7 min, $t_R$ (minor)=19.7 min. $^1$H NMR (500 MHz, CDCl$_3$) δ 9.93 (s, 1H), 7.81 (d, J=8.2 Hz, 2H), 7.51 (d, J=8.1 Hz, 2H), 5.17 (s, 1H), 3.78-3.73 (m, 1H), 3.67 (s, 3H), 2.73-2.67 (m, 2H). $^{13}$C NMR (126 MHz, CDCl$_3$) δ 191.91, 172.30, 149.46, 135.87, 129.99, 126.26, 69.81, 51.96, 43.00.

Example 27

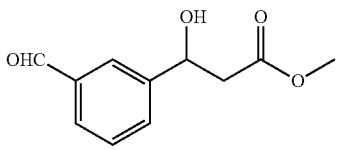

Methyl 3-(3-formylphenyl)-3-hydroxypropanoate (1s)

85% yield, $[\alpha]_D^{25}=-31.79$ (c=0.26 in CHCl$_3$), enantiomeric excess: 85%, Daicel Chiralpak AD, hexane/iso-propanol=90/10, flow rate 1.0 mL/min, 25° C.: $t_R$ (minor)=15.1 min, $t_R$ (major)=16.7 min. $^1$H NMR (500 MHz, CDCl$_3$) δ 10.00 (s, 1H), 7.89 (s, 1H), 7.79 (d, J=7.6 Hz, 1H), 7.65 (d, J=7.7 Hz, 1H), 7.52 (t, J=7.6 Hz, 1H), 5.21 (t, J=7.8 Hz, 1H), 3.72 (s, 3H), 3.58 (d, J=3.5 Hz, 1H), 2.80-2.71 (m, 2H). $^{13}$C NMR (126 MHz, CDCl$_3$) δ 192.10, 172.50, 143.74, 136.43, 131.74, 129.28, 129.14, 126.84, 69.64, 51.98, 42.97.

Example 28

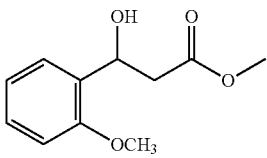

Methyl 3-hydroxy-3-(2-methoxyphenyl)propanoate (1t)

70% yield, $[\alpha]_D^{25}=-43.00$ (c=0.13 CHCl$_3$), enantiomeric excess: 85%, Daicel Chiralpak AD, hexane/iso-propanol=98/2, flow rate 1.0 mL/min, 25° C.: $t_R$ (minor)=28.4 min, $t_R$ (major)=30.4 min. $^1$H NMR (500 MHz, CDCl$_3$) δ 7.42 (d, J=7.5 Hz, 1H), 7.27-7.22 (m, 1H), 6.97 (t, J=7.4 Hz, 1H), 6.86 (d, J=8.2 Hz, 1H), 5.39-5.31 (m, 1H), 3.84 (s, 3H), 3.71 (s, 3H), 3.48 (d, J=4.2 Hz, 1H), 2.82 (dd, J=16.1, 3.4 Hz, 1H), 2.71 (dd, J=16.1, 9.3 Hz, 1H). $^{13}$C NMR (126 MHz, CDCl$_3$) δ 172.96, 156.04, 130.58, 128.60, 126.54, 120.82, 110.36, 66.55, 55.25, 51.71, 41.61.

Example 29

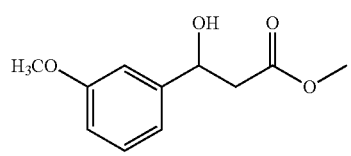

Methyl 3-hydroxy-3-(3-methoxyphenyl)propanoate (1u)

71% yield, $[\alpha]_D^{25}=-16.46$ (c=0.24 in CHCl$_3$), enantiomeric excess: 91%, Daicel Chiralpak AD, hexane/iso-propanol=95/5, flow rate 1.0 mL/min, 25° C.: $t_R$ (minor)=19.2 min, $t_R$ (major)=21.9 min. $^1$H NMR (500 MHz, CDCl$_3$) δ 7.26 (dd, J=10.2, 5.5 Hz, 1H), 6.93 (d, J=8.5 Hz, 2H), 6.82 (dd, J=8.1, 1.8 Hz, 1H), 5.10 (dd, J=9.0, 3.7 Hz, 1H), 3.80 (s, 3H), 3.71 (s, 3H), 3.36 (br, 1H), 2.72 (qd, J=16.3, 6.4 Hz, 2H). $^{13}$C NMR (126 MHz, CDCl$_3$) δ 172.70, 159.84, 144.29, 129.59, 117.90, 113.39, 111.17, 70.25, 55.22, 51.86, 43.22.

Example 30

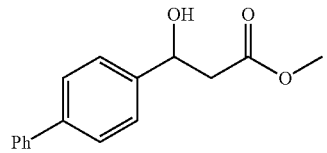 [SMILES: COC(=O)CC(O)c1ccc(-c2ccccc2)cc1]

Methyl 3-([1,1'-biphenyl]-4-yl)-3-hydroxypropanoate (1v)

72% yield, $[\alpha]_D^{25}=9.35$ (c=0.36 in CHCl$_3$), enantiomeric excess: 90%, Daicel Chiralpak AD, hexane/iso-propanol=90/10, flow rate 1.0 mL/min, 25° C.: $t_R$ (major)=12.6 min, $t_R$ (minor)=13.6 min. $^1$H NMR (500 MHz, CDCl$_3$) δ 7.62-7.56 (m, 4H), 7.48-7.41 (m, 4H), 7.35 (t, J=7.3 Hz, 1H), 5.24-5.17 (m, 1H), 3.75 (s, 3H), 3.26 (d, J=3.4 Hz, 1H), 2.80 (qd, J=16.4, 6.4 Hz, 2H). $^{13}$C NMR (126 MHz, CDCl$_3$) δ 172.75, 141.51, 140.84, 140.75, 128.78, 127.35, 127.33, 127.09, 126.12, 51.90, 43.10.

Example 31

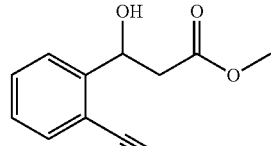

Methyl 3-(2-ethynylphenyl)-3-hydroxypropanoate
(1w)

75% yield, $[\alpha]_D^{25}=-45.20$ (c=0.24 in CHCl$_3$), enantiomeric excess: 82%, Daicel Chiralpak AD, hexane/iso-propanol=95/5, flow rate 1.0 mL/min, 25° C.: $t_R$ (minor)=14.7 min, $t_R$ (major)=16.5 min. $^1$H NMR (500 MHz, CDCl$_3$) δ 7.60 (d, J=7.8 Hz, 1H), 7.48 (d, J=7.6 Hz, 1H), 7.40 (t, J=7.6 Hz, 1H), 7.25 (t, 1H), 5.57 (d, J=9.7 Hz, 1H), 3.74 (s, 3H), 3.48 (d, J=3.1 Hz, 1H), 3.36 (s, 1H), 2.90 (dd, J=16.5, 2.7 Hz, 1H), 2.66 (dd, J=16.5, 9.8 Hz, 1H). $^{13}$C NMR (126 MHz, CDCl$_3$) δ 172.91, 144.85, 132.89, 129.38, 127.25, 125.29, 119.19, 82.79, 81.00, 68.26, 51.88, 41.95.

Example 32

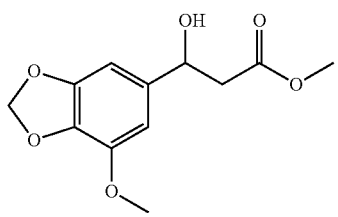 [SMILES: COC(=O)CC(O)c1cc(OC)c2c(c1)OCO2]

methyl-3-hydroxy-3-(7-methoxybenzo[d][1,3]dioxol-5-yl)propanoate (1x)

71% yield, $[\alpha]_D^{25}=-38.30$ (c=0.20 in CHCl$_3$), enantiomeric excess: 90%, Daicel Chiralpak AD, hexane/iso-propanol=95/5, flow rate 1.0 mL/min, 25° C.: $t_R$ (minor)=35.6 min, $t_R$ (major)=44.6 min. $^1$H NMR (500 MHz, CDCl$_3$) δ 6.57 (d, J=14.2 Hz, 2H), 5.96 (s, 2H), 5.04 (d, J=6.3 Hz, 1H), 3.90 (s, 3H), 3.73 (s, 3H), 3.20 (s, 1H), 2.70 (qd, J=16.3, 6.4 Hz, 2H). $^{13}$C NMR (126 MHz, CDCl$_3$) δ 172.66, 149.00, 143.67, 137.32, 134.75, 105.30, 101.49, 99.93, 70.32, 56.63, 51.89, 43.31.

Example 33

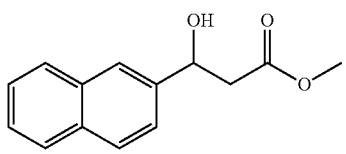 [SMILES: COC(=O)CC(O)c1ccc2ccccc2c1]

Methyl 3-hydroxy-3-(naphthalen-2-yl)propanoate
(1y)

81% yield, $[\alpha]_D^{25}=-13.56$ (c=0.23 in CHCl$_3$), enantiomeric excess: 91%, Daicel Chiralpak AD, hexane/iso-propanol=95/5, flow rate 1.0 mL/min, 25° C.: $t_R$ (minor)=23.6 min, $t_R$ (major)=25.8 min. $^1$H NMR (500 MHz, CDCl$_3$) δ 7.87-7.79 (m, 4H), 7.52-7.42 (m, 3H), 5.35-5.24 (m, 1H), 3.72 (d, J=7.5 Hz, 3H), 3.45 (d, J=2.9 Hz, 1H), 2.83 (qd, J=16.4, 6.4 Hz, 2H). $^{13}$C NMR (126 MHz, CDCl$_3$) δ 172.77, 139.88, 133.31, 133.06, 128.43, 128.03, 127.69, 126.25, 126.02, 124.47, 123.69, 70.46 (s), 51.92, 43.14.

Example 34

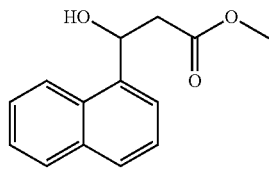 [SMILES: COC(=O)CC(O)c1cccc2ccccc12]

Methyl 3-hydroxy-3-(naphthalen-1-yl)propanoate
(1z)

82% yield, $[\alpha]_D^{25}=-53.54$ (c=0.13 in CHCl$_3$), enantiomeric excess: 86%, Daicel Chiralpak OD, hexane/iso-propanol=95/5, flow rate 1.0 mL/min, 25° C.: $t_R$ (major)=27.6 min, $t_R$ (minor)=40.2 min. $^1$H NMR (500 MHz, CDCl$_3$) δ 8.06 (d, J=8.3 Hz, 1H), 7.89 (d, J=7.9 Hz, 1H), 7.80 (d, J=8.2 Hz, 1H), 7.71 (d, J=7.1 Hz, 1H), 7.58-7.41 (m, 3H), 5.94 (d, J=9.6 Hz, 1H), 3.78 (s, 3H), 3.34 (d, J=3.1 Hz, 1H), 2.94 (dd, J=16.6, 2.9 Hz, 1H), 2.86 (dd, J=16.6, 9.7 Hz, 1H). $^{13}$C NMR (126 MHz, CDCl$_3$) δ 173.06, 137.97, 133.80, 129.97, 129.04, 128.35, 126.32, 125.64, 125.52, 122.95, 122.75, 67.37, 51.99, 42.56.

Example 35

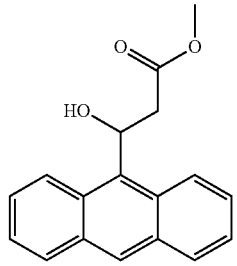 [SMILES: COC(=O)CC(O)c1c2ccccc2cc2ccccc12]

Methyl 3-(anthracen-9-yl)-3-hydroxypropanoate
(1aa)

78% yield, $[\alpha]_D^{25}=-21.63$ (c=0.26 in CHCl$_3$), enantiomeric excess: 76%, Daicel Chiralpak AD, hexane/iso-propanol=95/5, flow rate 1.0 mL/min, 25° C.: $t_R$ (minor)=27.5 min, $t_R$ (major)=30.7 min. $^1$H NMR (500 MHz, CDCl$_3$) δ 8.66 (s, 2H), 8.42 (s, 1H), 8.00 (d, J=8.3 Hz, 2H), 7.49 (dt, J=14.7, 6.9 Hz, 4H), 6.77 (dt, J=10.5, 2.7 Hz, 1H), 3.79 (s, 3H), 3.57 (dd, J=16.8, 10.7 Hz, 1H), 3.32 (d, J=2.8 Hz, 1H), 2.85 (dd, J=16.8, 3.1 Hz, 1H). $^{13}$C NMR (126 MHz, CDCl$_3$) δ 172.97, 132.28, 131.68, 129.38, 129.19, 128.57, 125.94, 124.85, 124.60, 77.29, 77.04, 76.78, 67.32, 52.00, 41.59.

Example 36

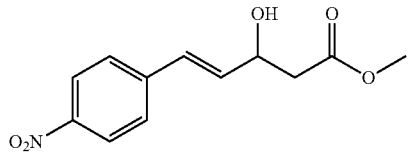 [SMILES: COC(=O)CC(O)/C=C/c1ccc([N+](=O)[O-])cc1]

Methyl (E)-3-hydroxy-5-(4-nitrophenyl)pent-4-enoate (1ab)

79% yield, $[\alpha]_D^{25}$=−18.12 (c=0.26 in CHCl$_3$), enantiomeric excess: 81%, Daicel Chiralpak OB, hexane/iso-propanol=85/15, flow rate 1.0 mL/min, 25° C.: $t_R$ (minor)=33.8 min, $t_R$ (major)=35.0 min. $^1$H NMR (500 MHz, CDCl$_3$) δ 8.18 (d, J=8.6 Hz, 2H), 7.51 (d, J=8.6 Hz, 2H), 6.77 (d, J=15.9 Hz, 1H), 6.41 (dd, J=15.9, 5.4 Hz, 1H), 4.78 (s, 1H), 3.75 (s, 3H), 3.23 (s, 1H), 2.72 (dd, J=16.5, 3.8 Hz, 1H), 2.64 (dd, J=16.5, 8.5 Hz, 1H). $^{13}$C NMR (126 MHz, CDCl$_3$) δ 172.42, 147.15, 142.96, 134.70, 128.55, 127.08, 124.00, 77.25, 77.00, 76.75, 68.26, 51.98, 40.94.

Example 37

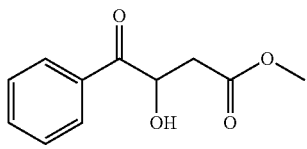

Methyl 3-hydroxy-4-oxo-4-phenylbutanoate (1ac)

71% yield, $[\alpha]_D^{25}$=+15.01 (c=0.12 in MeOH), enantiomeric excess: 90%, Daicel Chiralpak AS, hexane/iso-propanol=90/10, flow rate 1.0 mL/min, 25° C.: $t_R$ (major)=9.9 min, $t_R$ (minor)=12.0 min. $^1$H NMR (500 MHz, CDCl$_3$) δ 7.92 (d, J=7.5 Hz, 2H), 7.59 (t, J=7.4 Hz, 1H), 7.48 (t, J=7.7 Hz, 2H), 5.41 (d, J=5.0 Hz, 1H), 4.04 (s, 1H), 3.67 (s, 3H), 2.86 (dd, J=15.9, 3.4 Hz, 1H), 2.60 (dd, J=15.9, 8.0 Hz, 1H). $^{13}$C NMR (126 MHz, CDCl$_3$) δ 199.85, 170.90, 134.05, 133.42, 128.95, 128.64, 70.22, 52.06, 40.17.

Example 38

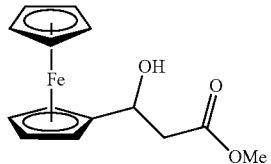

(1ad): 76% yield, $[\alpha]_D^{25}$=−13.32 (c=0.51 in CHCl$_3$), enantiomeric excess: 84%, Daicel AS, hexane/iso-propanol=90/10, flow rate 1.0 mL/min, 25° C.: $t_R$ (major)=11.1 min, $t_R$ (minor)=15.7 min. $^1$H NMR (500 MHz, CDCl$_3$) δ 4.85 (d, J=5.7 Hz, 1H), 4.27-4.12 (m, 9H), 3.73 (s, 3H), 2.79-2.70 (m, 2H), 2.66 (s, 1H). $^{13}$C NMR (126 MHz, CDCl$_3$) δ 172.39, 91.60, 68.56, 68.17, 68.11, 66.56, 66.47, 66.04, 51.81, 42.65, 29.71.

Example 39

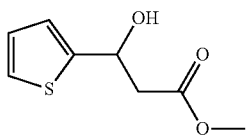

Methyl 3-hydroxy-3-(thiophen-2-yl)propanoate (1ae)

76% yield, $[\alpha]_D^{25}$=−13.56 (c=0.15 in CHCl$_3$), enantiomeric excess: 94%, Daicel Chiralpak OD, hexane/iso-propanol=95/5, flow rate 1.0 mL/min, 25° C.: $t_R$ (minor)=7.8 min, $t_R$ (major)=15.6 min. $^1$H NMR (500 MHz, MeOD) δ 7.30 (d, J=4.5 Hz, 1H), 6.99 (d, J=3.2 Hz, 1H), 6.94 (dd, J=4.8, 3.7 Hz, 1H), 5.33 (dd, J=7.6, 6.1 Hz, 1H), 3.67 (s, 3H), 2.83-2.78 (m, 2H). $^{13}$C NMR (126 MHz, MeOD) δ 172.89, 149.00, 127.61, 125.56, 124.68, 67.55, 52.22, 45.23.

Example 40

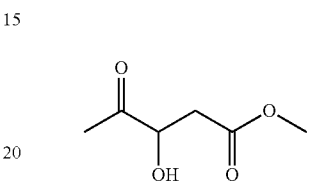

Methyl 3-hydroxy-4-oxopentanoate (1af)

70% yield $[\alpha]_D^{25}$=−11.01 (c=0.10 in hexane/iso-propanol=95/5, flow rate 1.0 mL/min, 25° C.: $t_R$ (major)=13.9 min, $t_R$ (minor)=18.7 min. $^1$H NMR (500 MHz, CDCl$_3$) δ 4.38 (d, J=5.5 Hz, 1H), 3.77 (d, J=4.8 Hz, 1H), 3.71 (s, 3H), 2.88 (dd, J=16.4, 4.2 Hz, 1H), 2.75 (dd, J=16.4, 6.3 Hz, 1H), 2.28 (s, 3H). $^{13}$C NMR (126 MHz, CDCl$_3$) δ 208.11, 171.23, 73.75, 52.10, 37.92, 25.26

Example 41

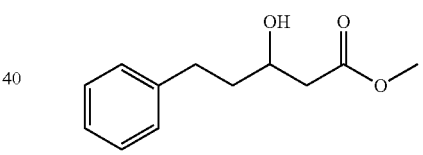

Methyl 3-hydroxy-5-phenylpentanoate (1ag)

72% yield, $[\alpha]_D^{25}$=+18.97 (c=0.26 in CHCl$_3$), enantiomeric excess: 77%, Daicel Chiralpak OB, hexane/iso-propanol=95/5, flow rate 1.0 mL/min, 25° C.: $t_R$ (minor)=15.5 min, $t_R$ (major)=16.9 min. $^1$H NMR (500 MHz, CDCl$_3$) δ 7.26-7.03 (m, 5H), 4.08-3.84 (m, 1H), 3.63 (s, 3H), 2.79-2.70 (m, 1H), 2.66-2.59 (m, 1H), 2.41 (qd, J=16.5, 6.0 Hz, 2H), 1.82-1.71 (m, 1H), 1.71-1.63 (m, 1H). $^{13}$C NMR (126 MHz, CDCl$_3$) δ 173.33, 141.70, 128.45, 128.43, 125.91, 67.25, 51.73, 41.16, 38.12, 31.76.

The above is only the preferred embodiment of the present invention, and the scope of the present invention is not limited thereto, and thus equivalent changes made in the claims of the present invention are still within the scope of the present invention.

What is claimed is:
1. A method for synthesizing a chiral β-hydroxy acid ester compound, comprising the steps of:
using an aldehyde compound and a monoalkyl malonate as raw materials;

using a metal compound, an organic acid salt and a chiral ligand as a catalyst to make the raw materials carry out decarboxylation aldol addition reaction in an organic solvent;

performing separation and purification to obtain a chiral β-hydroxy acid ester compound after the reaction is completed, wherein the chiral β-hydroxy acid ester compound has the structural formula as below:

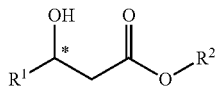

wherein said aldehyde compound has the structural formula as below:

wherein said monoalkyl malonate has the structural formula as below:

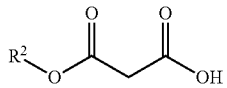

wherein said $R^1$ is selected from one of the group consisting of an alkyl group, a substituted phenyl group or an aryl group having a fluorine, a chlorine, a bromine, a nitro group, an alkyl group and an alkoxy group;

wherein said $R^2$ is selected from one of the group consisting of a methyl, an ethyl, a propyl, a butyl, an isopropyl and a tert-butyl;

wherein said organic solvent used is an organic solvent that does not react with reactants and products.

2. The method according to claim 1, wherein said organic solvent is selected from one or a combination of dichloromethane, ethyl acetate, tetrahydrofuran, acetonitrile, toluene, methanol and chloroform.

3. The method according to claim 1, wherein the mass of said organic solvent used is 1-200 times the mass of the raw materials.

4. The method according to claim 1, wherein the molar ratio of said aldehyde compound to said monoalkyl malonate is 1:1-5.

5. The method according to claim 1, wherein said metal compound in said catalyst is selected from the group consisting of one or a combination of copper triflate, copper sulfate, copper acetate, palladium acetate, ferrous fluoride, silver acetate, nickel acetate tetrahydrate, nickel acetylacetonate, nickel fluoride, nickel chloride hexahydrate, nickel sulfate, nickel perchlorate, and bistriphenylphosphine nickel chloride.

6. The method according to claim 1, wherein said chiral ligand in said catalyst is selected from one or a combination of the following:

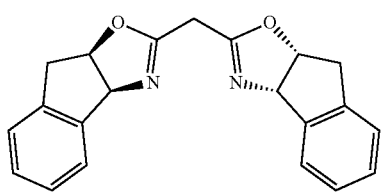
L1

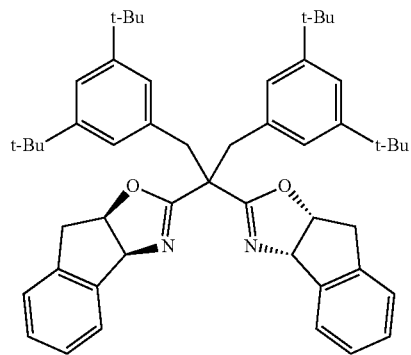
L2

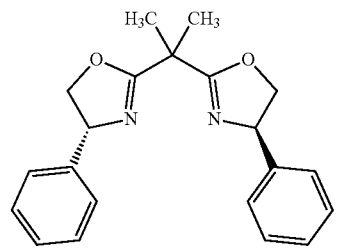
L3

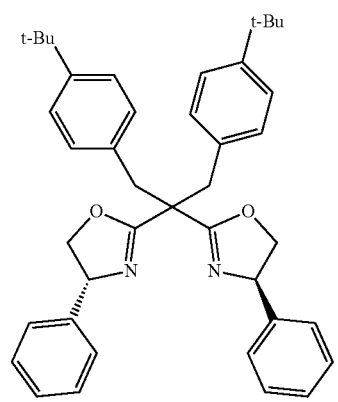
L4

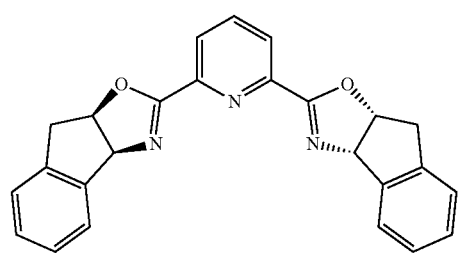
L5

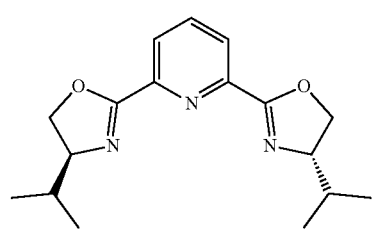
L6

-continued

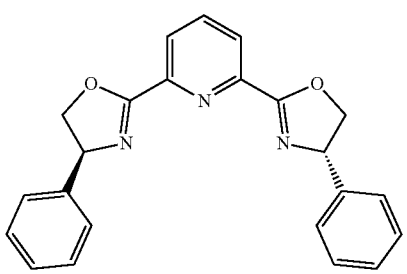

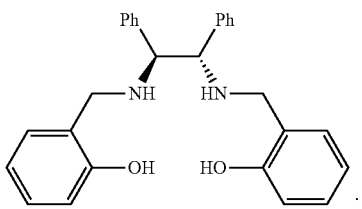

7. The method according to claim 1, wherein the organic acid salt in said catalyst is selected from one or a combination of the following:

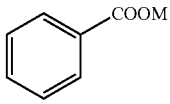
M = Li, Na, K, Ru, Cs

M = Li, Na, K, Ru, Cs

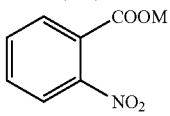
M = Li, Na, K, Ru, Cs

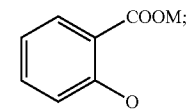
M = Li, Na, K, Ru, Cs wherein the molar ratio of metal to salt in said catalyst is 1:1-3.

8. The method according to claim 1, wherein the ratio of said catalyst to said aldehyde compound is 1 wt %-20 wt %, and the molar ratio of the metal to the chiral ligand in said catalyst is 1:1-1.5.

9. The method according to claim 1, wherein said decarboxylation aldol addition reaction has a temperature of 0-60° C.

10. The method according to claim 2, wherein said decarboxylation aldol addition reaction has a reaction time of 3-120 hours.

* * * * *